United States Patent [19]
Dodge

[11] Patent Number: 5,596,004
[45] Date of Patent: Jan. 21, 1997

[54] METHODS OF INHIBITING MALE INFERTILITY

[75] Inventor: Jeffrey A. Dodge, Indianapolis, Ind.

[73] Assignee: Eli Lilly and Company, Indianapolis, Ind.

[21] Appl. No.: 168,482

[22] Filed: Dec. 21, 1993

[51] Int. Cl.$^6$ ................................................. A61K 31/445
[52] U.S. Cl. ........................... 514/324; 514/317; 514/319; 514/320
[58] Field of Search ................................... 514/317, 319, 514/320, 324

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |

FOREIGN PATENT DOCUMENTS

| | | |
|---|---|---|
| WO93/10113 | 5/1993 | WIPO. |
| WO93/1074 | 6/1993 | WIPO. |

OTHER PUBLICATIONS

Buvat, J. et al., Antiestrogens as Treatment of Female and Male Infertilities, Hormone Res. vol. 28 No. 2–4, pp. 219–229, 1987.

Lewis-Jones, D. T. et al., Improvement in Semen Quality in Infertile Males after Treatment with Tamoxifen, Andrologia, vol. 19, No. 1, pp. 86–90, 1987.

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti-estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti-Estrogen, Simulates the Effects of Estrogen in Inhibiting Bone Resorption Through Regulating TGFB-3 Expression in Bone;". Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properties of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

(List continued on next page.)

*Primary Examiner*—Shailendra Kumar
*Attorney, Agent, or Firm*—James J. Sales

[57] ABSTRACT

A method of inhibiting male infertility comprising administering to a human in need thereof an effective amount of a compound having the formula

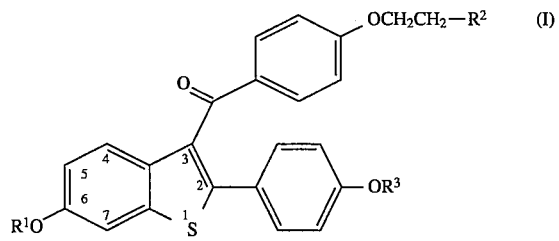

wherein $R^1$ and $R^3$ are independently hydrogen, —$CH_3$,

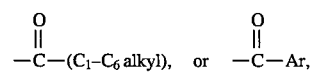

wherein Ar is optionally substituted phenyl;

$R^2$ is selected from the group consisting of pyrrolidine, hexamethyleneamino, and piperidino; or a pharmaceutically acceptable salt of solvate thereof.

4 Claims, No Drawings

OTHER PUBLICATIONS

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl] [4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Cigorraga et al., "Estrogen Dependence of a Gonadotropin––induced Steroidogenic Lesion in Rat Testicular Leydig Cells", *J. Clin Invest*, 65, 699–705, Mar. 1980.

METHODS OF INHIBITING MALE INFERTILITY

BACKGROUND OF THE INVENTION

An estimated one in five couples in the United States has some degree of infertility. Infertility is defined as the inability of a heterosexual couple to achieve a pregnancy within one year of unprotected intercourse (Cecil Textbook of Medicine, W. B. Saunders Company, 19th Ed., p. 1339–1340, (1992)). Major etiological factors include ovulatory dysfunction, abnormal tubal function, cervical factors, and male sperm factors. (The Merck Manual of Diagnosis and Therapy, Merck Research Laboratories, 16th Ed., p. 1768–1770, (1992)). An estimated five to six percent of men in the reproductive age group are infertile. Most causes of male infertility are due to an abnormal sperm count or low semen quality.

A majority of problems associated with fertility in males stem from changes in testosterone levels. In particular, decreases in concentration of this steroid can result in infertility and impotence. Endogenous estrogen has been well-documented to serve as a regulatory factor in testosterone production by interaction with the estrogen receptor (Nozu, K. et al., *J. Biol. Chem.* 256, 1915 (1981); Brinkman, A. et al., *Endocrinology*, 110, 1834 (1982)). Thus, intratesticular estrogen plays a key role in testosterone steroidogenisis with increased levels of estrogen inhibiting testosterone production (Cigorraga, S. B. et al., *J. Clin. Invest.* 65, 699 (1982); Padron, R. S. J., *Clin. Endocrinol. Metab.* 50, 1100 (1980)). A need exists for new methods of treating or preventing male infertility.

SUMMARY OF THE INVENTION

This invention provides methods for inhibiting male infertility comprising administering to a human in need thereof an effective amount of a compound of formula I

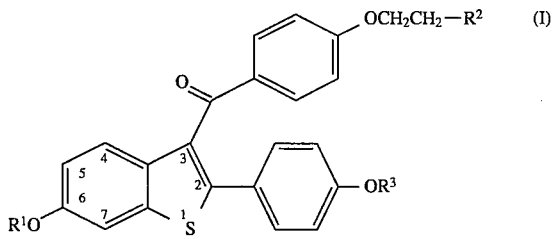

wherein $R^1$ and $R^3$ are independently hydrogen, —$CH_3$,

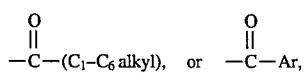

wherein Ar is optionally substituted phenyl;
$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting male infertility. The methods of treatment provided by this invention are practiced by administering to a human in need thereof a dose of a compound of formula I or a pharmaceutically acceptable salt or solvate thereof, that is effective to inhibit male infertility. The term inhibit is defined to include its generally accepted meaning which includes prophylactically treating a human subject to incurring the problem described, and holding in check and/or treating an existing problem. As such, the present method includes both medical therapeutic and/or prophylactic treatment, as appropriate.

Raloxifene, a preferred compound of this invention, is the hydrochloride salt of a compound of formula 1, wherein $R^1$ and $R^3$ are hydrogen and $R^2$ is 1-piperidinyl, and is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each. It is believed that the compounds described herein act to block the inhibitory properties of estrogen on testosterone production.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418, 068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit male infertility according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively treat the problem.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

FORMULATIONS

In the formulations which follow, "active ingredient" means a compound of formula I.

Formulation 1: Gelatin Capsules
Hard gelatin capsules are prepared using the following

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound of formula 1 wherein $R^2$ is piperidino, (raloxifene), that have been made include those shown below:

| Ingredient | Quantity (mg/capsule) |
|---|---|
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |

-continued

Formulation 6: Tablets

| Ingredient | Quantity (mg/tablet) |
|---|---|
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
|---|---|
| Active Ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

ASSAYS

Assay I

The following assay is described in Cigorraga et al., *J. Clin Invest*, 65, 699–705, March 1980, incorporated herein by reference.

Five to fifty male rats (200–250 g) are obtained. Gonadotropin-induced desensitization of Leydig cells is achieved by intravenous injection of hCG or by subcutaneous injection of GnRH. A compound of formula 1 is administered with the intravenous hCG dose or alone in controls and before subcutaneous administration of LH releasing-hormone. Animals are killed by decapitation 2 or 3 days after injection of gonadotropin or GnRH, and interstitial cells from testes of normal and treated animals are prepared by collagenase digestion. The cells are further fractionated by density gradient centrifugation, giving purified cell preparations containing over 90% Leydig cells as judged by morphological criteria and metabolic responses. The purified Leydig cells are washed once and resuspended in a medium containing 0.1% bovine serum albumin. The proportion of incubation medium to cells is equivalent to 2 ml/testis, giving about $10^6$ purified Leydig cells/ml.

Leydig cells are incubated with purified hCG or dibutyryl cyclic (c)AMP ($Bt_2$cAMP). When pregnenolone accumulation is to be measured, inhibitors of 3β-hydroxysteroid dehydrogenase and 17-hydroxylase are added to cell incubations before the addition of stimuli; control incubations ware treated similarly.

Groups of rats are also studied after the following treatments (a) control; (b) intravenous injection of hCG; (c) intravenous injection of hCG plus a compound of formula 1 and i.m.; (d) subcutaneous injections of hCG. The rats are killed at selected times ater the injections. Blood samples collected from the decapitated animals are allowed to clot, and serum is stored at −70° C. before testosterone analysis. Testes are removed and kept frozen until analyzed for estradiol 17β, testosterone, progesterone, and 17α-hydroxyprogesterone.

Assays of Steroids and Serum hCG

Decapsulated testes are homogenized in PBS/testis and extracted with ethyl acetate after addition of tracer amounts of H-steroids to account for losses during the fractionation procedure. Testosterone is measured and the testosterone content of testis extracts and serum is determined after isolation of the steroid. Pregnenolone is measured with a highly specific rabbit antiserum to the 11-hemisuccinate albumin conjugate. Radioimmunoassay of 17α-hydroxyprogesterone is performed with an antiserum to the 3-carboxymethyloxime derivative. 17β-estradiol assays are performed using a highly specific rabbit antiserum to 6-Ketoestradiol conjugated to bovine serum albumin. Immunoreactive serum hCG concentrations are measured.

Assay of LH Receptors in Dispersed Leydig Cells

Radioiodinated hCG tracer is prepared by lactoperoxidase method and purified by sepharose-concanavalin A chromatography. Purified Leydig cells ($5 \times 10^5$) are incubated for 3 h at 34° C. with $5 \times 10^5$ dpm of $^{125}$I-hCG (Specific activity 40 µCi/µg) with additions of hCG to ensure receptor saturation. Nonspecific binding is determined by incubation of cells with the labeled hormone in the presence of unlabeled hCG. All binding capacities are, calculated for replicate estimations of specific $^{125}$I-hCG binding at saturation, with corrections for specific activity and maximum bindability of the tracer preparation. The mean binding capacity is calculated for each of the experimental groups and expressed as a percentage of control values, or as the number of receptor sites per cell.

Increases in the cellular LH receptors and/or testosterone responses, or prevention of reduction of maximal testosterone response in Leydig cells from hCG-desensitized animals, illustrate the activity of the compounds of formula 1.

Assay II

Five to fifty men are selected for the clinical study. The men are are in good general health, but suffer from infertility. The study has a placebo control group, i.e., the men are divided into two groups, one of which receives the active agent of this invention and the other receives a placebo. All men in the study have their sperm benchmarked for quality and quantity. Men in the test group receive between 50–200 mg of the active agent per day by the oral route. They continue this therapy for 3–12 months. Accurate records are kept as to the benchmarks in both groups and at the end of the study these are compared. The results are compared both between members of each group and also the results for each patient are compared to the benchmarks of each patient before the study began.

Utility of the compounds of the invention is illustrated by the positive impact they have in at least one of the above assays.

We claim:

1. A method of inhibiting male infertility comprising administering to a human in need thereof an effective amount of a compound having the formula

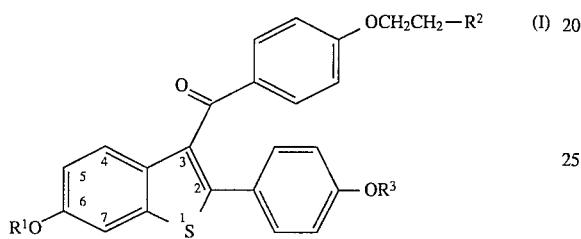 (I)

wherein $R^1$ and $R^3$ are independently hydrogen, $-CH^3$,

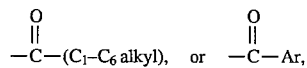

wherein Ar is optionally substituted phenyl;
$R^2$ is piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said compound is

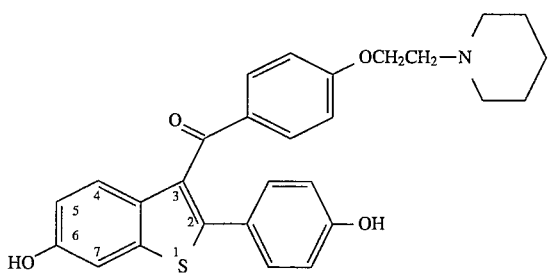

or its hydrochloride salt.

* * * * *